(12) United States Patent
Manzella, Jr. et al.

(10) Patent No.: US 9,022,344 B2
(45) Date of Patent: May 5, 2015

(54) CLAMPING SYSTEMS AND APPARATUS

(75) Inventors: Salvatore Manzella, Jr., Barrington, IL (US); Richard L. West, Lake Villa, IL (US); Gregory G. Pieper, Waukegan, IL (US)

(73) Assignee: Fenwal, Inc., Lake Zurich, IL (US)

( * ) Notice: Subject to any disclaimer, the term of this patent is extended or adjusted under 35 U.S.C. 154(b) by 587 days.

(21) Appl. No.: 13/404,132

(22) Filed: Feb. 24, 2012

(65) Prior Publication Data

US 2012/0216891 A1 Aug. 30, 2012

Related U.S. Application Data

(60) Provisional application No. 61/447,446, filed on Feb. 28, 2011.

(51) Int. Cl.
*F16K 7/04* (2006.01)
*A61M 39/28* (2006.01)
*F16L 37/56* (2006.01)
*F16K 31/06* (2006.01)

(52) U.S. Cl.
CPC .............. *F16K 7/045* (2013.01); *A61M 39/281* (2013.01)

(58) Field of Classification Search
CPC .............................. F16K 7/045; A61M 39/281
USPC .......... 137/594, 861, 871, 595; 604/4.01, 6.1; 251/4, 7
See application file for complete search history.

(56) References Cited

U.S. PATENT DOCUMENTS

| | | | | |
|---|---|---|---|---|
| 2,471,623 A | * | 5/1949 | Hubbell | .................... 137/625.18 |
| 2,531,802 A | * | 11/1950 | Boyer | ......................... 210/428 |
| 2,645,245 A | * | 7/1953 | Maisch | .................... 137/565.35 |
| 2,985,192 A | * | 5/1961 | Taylor et al. | ................ 137/627.5 |
| 3,075,551 A | * | 1/1963 | Smith et al. | .................... 137/595 |
| 3,550,619 A | * | 12/1970 | Halasz et al. | .................... 137/595 |
| 3,882,899 A | * | 5/1975 | Ginsberg et al. | ............ 137/627.5 |
| 3,932,065 A | * | 1/1976 | Ginsberg et al. | .............. 417/317 |
| 4,524,802 A | * | 6/1985 | Lawrence et al. | ............. 137/595 |
| 4,653,719 A | * | 3/1987 | Cabrera et al. | ..................... 251/7 |
| 5,188,334 A | * | 2/1993 | Yoshii et al. | ....................... 251/7 |
| 5,584,320 A | | 12/1996 | Skinkle | |
| 5,765,591 A | | 6/1998 | Wasson | |
| 5,769,385 A | | 6/1998 | Burrous | |
| 7,150,585 B2 | * | 12/2006 | Kleineidam et al. | ............ 406/50 |
| 7,442,178 B2 | | 10/2008 | Chammas | |
| 7,476,209 B2 | | 1/2009 | Gara | |
| 7,559,524 B2 | | 7/2009 | Gray | |
| 2004/0127840 A1 | | 7/2004 | Gara | |
| 2008/0142157 A1 | | 6/2008 | Maltezos | |
| 2009/0286221 A1 | | 11/2009 | Klip et al. | |
| 2009/0320937 A1 | | 12/2009 | Arnett | |

FOREIGN PATENT DOCUMENTS

EP 1 512 420 A2 9/2005

* cited by examiner

*Primary Examiner* — Craig Schneider
*Assistant Examiner* — Josephine Trinidad-Borges
(74) *Attorney, Agent, or Firm* — Cook Alex Ltd.

(57) ABSTRACT

A clamping apparatus is provided for use with a fluid flow device, such as a blood separation system. The clamping apparatus includes a clamp head at least partially defining first and second tube openings each to receive tubing. The clamping apparatus also includes a first actuator coupled to a first flow control member. The first flow control member is configured to be movable via the first actuator relative to the first tube opening to control fluid flow through tubing located in the first tube opening. The clamping apparatus further includes a second actuator coupled to a second flow control member. The second flow control member is movable via the second actuator relative to the second tube opening to control fluid flow through tubing located in the second tube opening.

19 Claims, 9 Drawing Sheets

CLAMPING SYSTEMS AND APPARATUS

This application claims priority from and the benefit of U.S. provisional patent application Ser. No. 61/447,446, filed Feb. 28, 2011, which is hereby incorporated herein by reference.

BACKGROUND

1. Field of the Disclosure

The present disclosure relates to occlusion systems. More particularly, the present disclosure relates to occlusion systems for fluid separators.

2. Description of Related Art

Techniques for the separation and collection of given constituents of whole blood are in wide use for many therapeutic, medical, and experimental applications. In blood separation procedures, one or more blood constituents, such as plasma, may be collected from individual donors by withdrawing whole blood, separating the targeted constituent(s), and returning the remaining constituents to the donor. Plasmapheresis may be carried out by various techniques, including by centrifugation and by membrane filtration. One method of plasmapheresis by membrane filtration is described in U.S. Pat. No. 5,194,145 to Schoendorfer, which is hereby incorporated herein by reference. A cylindrical, membrane-covered spinner having an interior collection system is disposed within a stationary shell or housing, with a substantially annular gap, or space separating the membrane and the shell. Blood is fed into the gap at an inlet of the device and, as the spinner is rotated about its central axis, the blood moves both circumferentially and generally axially through the gap. Plasma is extracted through the membrane to a central flow path inside the spinner, where it is removed from an outlet of the device. The remaining blood constituents are removed from the device at another outlet associated with the gap. Plasma extraction in this device is enhanced by the formation of Taylor vortices at and around the membrane, which arise upon rotation of the spinner within the shell, as described in greater detail in the Schoendorfer '145 patent. Plasmapheresis methods and systems can also include tubing, pumps, and components as described in U.S. Pat. No. 4,888,004 to Williamson, which is hereby incorporated herein by reference.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately as set forth in the claims appended hereto.

According to one aspect of the present disclosure, a clamping apparatus is provided for use with a fluid flow device. The apparatus includes a clamp head at least partially defining first and second tube openings each to receive tubing. The apparatus also includes a first actuator coupled to a first flow control member, with the first flow control member being configured to be movable via the first actuator relative to the first tube opening to control fluid flow through a first tube when located therein. The apparatus further includes a second actuator coupled to a second flow control member, with the second flow control member being movable via the second actuator relative to the second tube opening to control fluid flow through a second tube when located therein.

According to another aspect of the present disclosure, a system is provided for occluding fluid in one or more fluid pathways. The system includes a first tube opening for receiving a portion of a first tube comprising a first fluid pathway and a second tube opening for receiving a portion of a second tube comprising a second fluid pathway. The system also includes a first actuator coupled to a first linear drive mechanism and a second actuator coupled to a second linear drive mechanism. A first anvil is coupled to the first linear drive mechanism, while a second anvil is coupled to the second linear drive mechanism. The first actuator is configured to move the first linear drive mechanism and the first anvil to restrict the first tube opening and at least partially occlude the first tube opening. The second actuator is configured to move the second linear drive mechanism and the second anvil to restrict the second tube opening and at least partially occlude the second tube opening.

DESCRIPTION OF THE ILLUSTRATED EMBODIMENTS

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

Example systems for occluding fluid pathways are disclosed. Systems according to the present disclosure may enable multiple configurations for occlusion of various fluid pathways in a fluid flow device. For illustrative purposed, occlusive devices according to the present disclosure will be described herein as they may be applied to or used in combination with fluid or blood processing or separation system, but it should be understood that occlusive devices of the type described herein are not limited to use in any particular fluid flow device, unless otherwise indicated.

In one embodiment, an example occlusion device, system, or apparatus includes a binary clamp having a plurality of tube openings formed in a clamp head. The tube openings may be configured to receive a portion of a tube used in blood separation. The clamp may include actuators or power sources, such as solenoids or pneumatic or hydraulic power sources. The clamp may further include movable members connected to linear mechanisms. Upon activation of the actuators, which may be independently operable, the movable members may drive clamp anvils by way of the linear mechanisms to control the size of the tube openings and fluid flow therethrough. As used herein, the term "binary" may be understood to refer to a clamp having two tube openings and separate tubes passing through each tube opening, with the clamp allowing fluid flow through only one of the tubes at a time. For example, such a clamp could be configured to move between first and second conditions or states, with a first tube opening being open (to allow fluid flow through a tube received in the first tube opening) and a second tube opening being closed (to prevent fluid flow through a tube received in the second tube opening) in the first condition or state, but with the first tube opening being closed and the second tube opening being open in the second condition.

Figure 1:
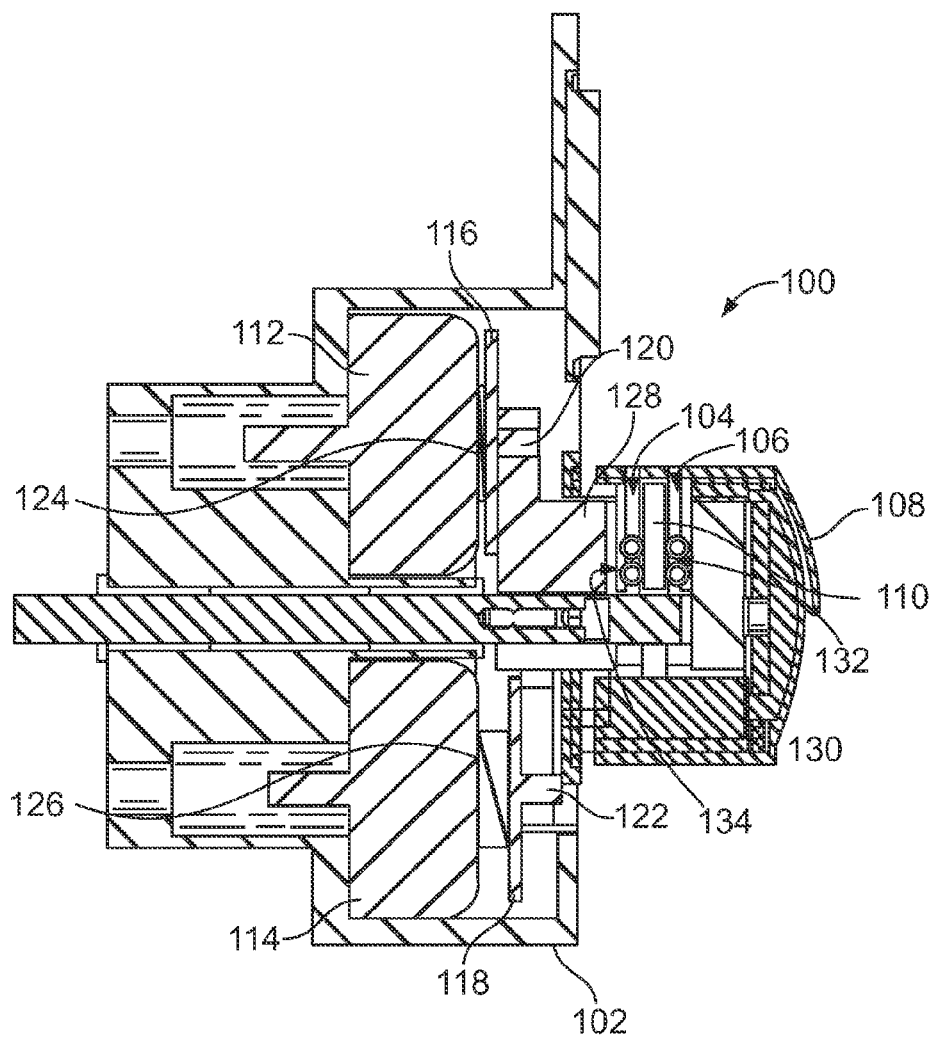
FIGS. 1-4 are cross-sectional views of an example occlusion device according to an aspect of the present disclosure, with the occlusion device in different positions or conditions.

FIG. 1 depicts a fluid pathway occlusion system or apparatus 100 (e.g., binary or dual clamp) that enables the occlusion of various fluid pathways in tubing. The system 100 may be used in connection with blood collection and/or processing systems, or any other suitable device, including other fluid pump systems or processes outside the blood industry. System 100 includes a housing 102 (e.g., frame, body portion, base, mounting structure, structure, support, etc.) which is configured to attach to a fluid flow system. In one embodiment, the fluid flow system may be a blood separation device, such as an AUTOPHERESIS-C® system, an AMICUS® system, or an ALYX® system, each available from Fenwal, Inc. of Lake Zurich, Ill.

System 100 may include a plurality of tube openings, such as passageways or slots 104 and 106 (e.g., apertures, grooves, etc.) formed in a body portion or clamp head 108. The tube openings 104 and 106 are configured to receive a portion of a tube such as for use in a blood separation system. A divider or separator 110 divides and/or separates the first tube opening 104 from the second tube opening 106. In the illustrated embodiment, the system 100 is illustrated with two tube openings, but it is within the scope of the present disclosure for a different number of tube openings and associated actuators and fluid flow assemblies to be employed.

System 100 may also include one or more electrical, pneumatic, or hydraulic actuators or power sources, such as solenoids 112 and 114, which may include movable members or portions 116 and 118 (respectively) connected to linear shafts 120 and 122 (e.g., mechanisms, slides, etc.). As further described below, upon activation of solenoid 112, the associated movable member 116 drives an associated clamp anvil or fluid control member or plunger or flow control member 128 by way of linear shaft 120 to control tube opening 104. Similarly, upon activation of solenoid 114, the associated movable member 118 drives an associated clamp anvil or fluid control member or plunger or flow control member 130 by way of linear shaft 122 to control tube opening 106. The solenoids 112 and 114 may be activated substantially simultaneously or separately.

More particularly, in one embodiment, each solenoid 112, 114 moves the associated anvil 128, 130 relative to the divider 110 to enable and/or substantially prevent fluid flow through tubing 132, 134 positioned within the corresponding tubing opening 104, 106. Thus, the anvils 128 and 130 are movable to control (e.g., increase, decrease) fluid flow through the tubing openings 104 and 106. One or both of the solenoids 112 and/or 114 may include a cylindrical coil of wire, or other suitable element, which generates magnetic force when an electrical current is applied, thereby moving the anvils 128 and/or 130 toward or away from tube openings 104 and/or 106 in connection with solenoid springs 124 and/or 126. It may be preferred for the actuator systems and their corresponding components (e.g., the solenoids, anvils, and solenoid springs) to be similarly configured, but it is also within the scope of the present disclosure for the actuator systems to be different configured.

In one position or condition, which is depicted in FIG. 1, the fluid pathway occlusion system 100 is in an open-open configuration in which tube openings 104 and 106 are both open (i.e., clamp anvils 128 and 130 are spaced away from the divider 110 and not blocking openings 104 and 106). The open-open state enables a user to freely load tubing into clamp head 108 without manipulating any either clamp anvil 128, 130. In one embodiment, which is shown in FIG. 1, solenoid 112 is energized to counter the force of solenoid spring 124, thereby drawing member 116 toward solenoid 112. Linear shaft 120 is connected to member 116 and anvil 128. Therefore, such movement of member 116 also draws linear shaft 120 and anvil 128 toward solenoid 112, thereby leaving opening 104 unrestricted. This configuration also acts as a failsafe and enables occlusion of opening 104 in the event of a power failure (as described in connection with FIG. 2).

In the illustrated embodiment of FIG. 1, solenoid 114 is not energized and the force of solenoid spring 126 pushes member 118 away from solenoid 114. Linear shaft 122 is coupled (e.g., operably coupled) and/or connected to member 118 and anvil 130. Therefore, such movement of member 118 also pushes linear shaft 122 and anvil 130 away from solenoid 114, thereby leaving opening 106 unrestricted.

With tube openings 104 and 106 open, a user may load tubing as part of a fluid flow application, such as a blood collection and/or separation procedure. System 100 simplifies the loading process compared to clamp systems that utilize only a single tube opening. For example, users can advantageously load a plurality of tubes into a single clamp system (e.g., the tube opening 104 or the tubing opening 106) as described herein, rather than loading two tubes into two separate clamp systems, as in conventional clamp systems. The multiple clamp system described herein also requires less space (e.g., footprint) in a fluid flow device and therefore enables smaller overall system size and increased portability.

Figure 2:
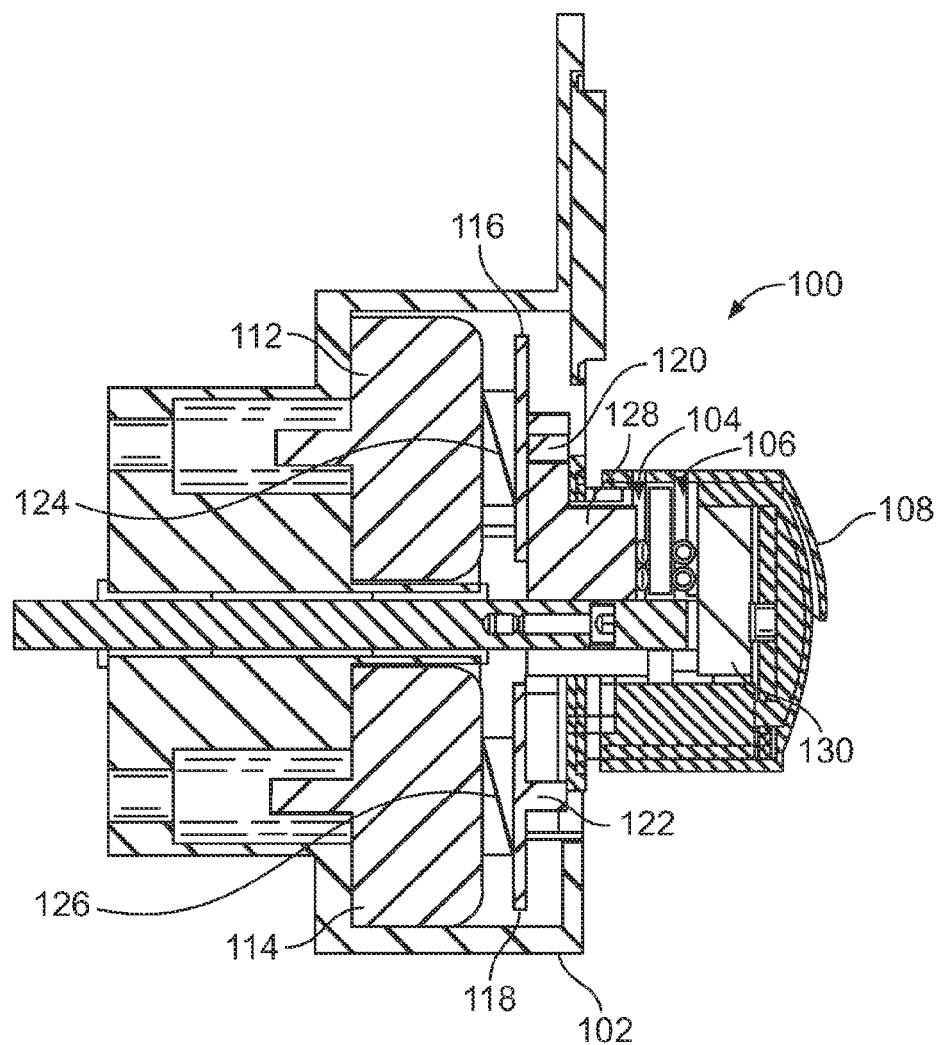

FIG. 2 shows fluid pathway occlusion system 100 in a closed-open configuration in which tube opening 104 is closed (e.g., clamp anvil 128 is blocking opening 104) and tube opening 106 is open (e.g., clamp anvil 130 is not blocking opening 106). In one embodiment, solenoid 112 is not energized and the force of solenoid spring 124 pushes member 116 away from solenoid 112. Linear shaft 120 is connected to member 116 and anvil 128. Therefore, movement of member 116 also pushes linear shaft 120 and anvil 128 away from solenoid 112 into opening 104 and restricts the flow of fluid through any tube loaded therein. When opening 104 is blocked by anvil 128, a seal is formed which prevents fluid from passing freely through tubing positioned in opening 104. Hence, as described above for the illustrated embodiment, power failures result in the occlusion of opening 104.

Similar to the condition of FIG. 1, the solenoid 114 is not energized in FIG. 2 and the force of solenoid spring 126 pushes member 118 away from solenoid 114. Linear shaft 122 is connected to member 118 and anvil 130. Therefore, movement of member 118 also pushes linear shaft 122 and anvil 130 away from solenoid 114, thereby leaving opening 106 unrestricted.

Figure 3:
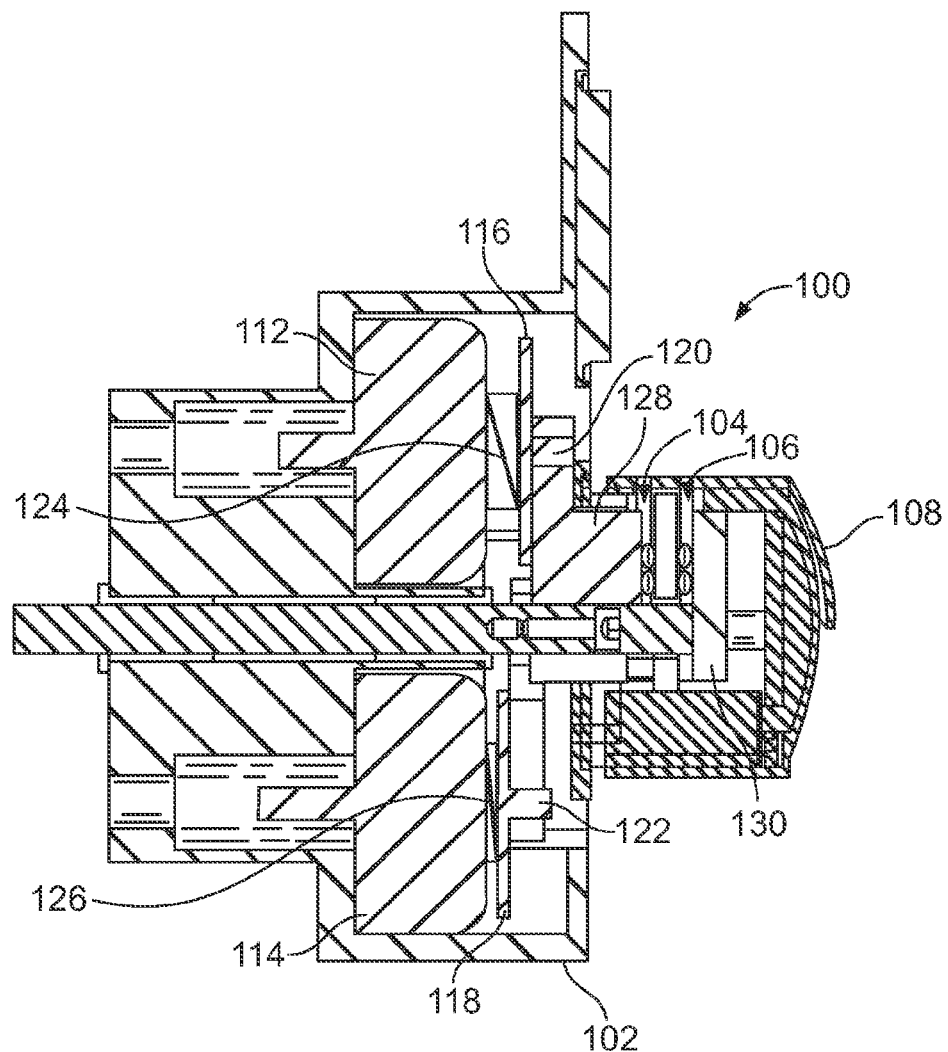

FIG. 3 shows fluid pathway occlusion system 100 in a closed-closed configuration in which tube opening 104 is closed (e.g., clamp anvil 128 is blocking opening 104) and tube opening 106 is closed (e.g., clamp anvil 130 is blocking opening 106). As shown in FIG. 3, solenoid 112 is not energized and the force of solenoid spring 124 pushes member 116 away from solenoid 112. Linear shaft 120 is connected to member 116 and anvil 128. Therefore, movement of member 116 also pushes linear shaft 120 and anvil 128 away from solenoid 112 into opening 104, thereby compressing and restricting any tube loaded therein. As shown in FIG. 3, solenoid 114 is energized to counter the force of solenoid spring 126, thereby drawing member 118 toward solenoid 114. Linear shaft 122 is connected to member 118 and anvil 130. Therefore, movement of member 118 also pulls linear shaft 122 and anvil 130 in the direction of solenoid 114, thereby drawing anvil 130 into opening 106 and restricting any tube loaded therein.

Figure 4:
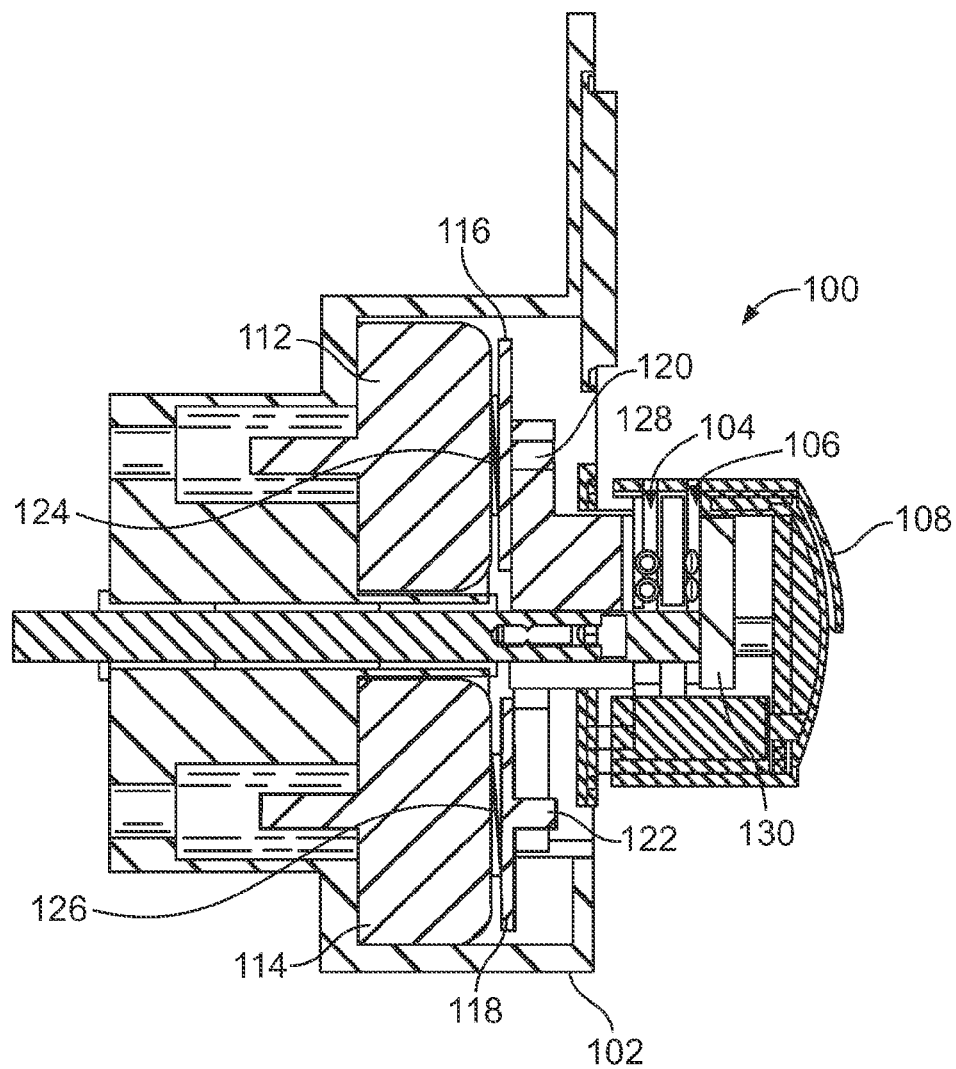

FIG. 4 shows fluid pathway occlusion system 100 in an open-closed configuration in which tube opening 104 is open (e.g., clamp anvil 128 is not blocking opening 104) and tube opening 106 is closed (e.g., clamp anvil 130 is blocking opening 106). As shown in FIG. 4, solenoid 112 is energized to counter the force of solenoid spring 124, thereby drawing member 116 toward solenoid 112. Linear shaft 120 is connected to member 116 and anvil 128. Therefore, movement of member 116 also draws linear shaft 120 and anvil 128 toward solenoid 112, thereby leaving opening 104 unrestricted. When opening 104 is not blocked by anvil 128, fluid may pass freely through tubing positioned in opening 104.

As shown in FIG. 4, solenoid 114 is energized to counter the force of solenoid spring 126, thereby drawing member 118 toward solenoid 114. Linear shaft 122 is connected to member 118 and anvil 130. Therefore, movement of member 118 also pulls linear shaft 122 and anvil 130 in the direction of solenoid 114, thereby drawing anvil 130 into opening 106 and restricting any tube loaded therein. When opening 106 is blocked by anvil 130, a seal is formed which prevents fluid from passing freely through tubing positioned in opening 106.

While the foregoing description illustrates one embodiment of an occlusion system according to the present disclosure, modifications may be made without departing from the scope of the present disclosure. For example, rather than the first actuator 112 being configured to occlude the associated tube opening upon power failure (or deactivation of the actuator), the first actuator 112 may alternatively be configured to open the associated tube opening upon power failure or deactivation of the actuator. Similarly, rather than the second actuator 114 being configured to open the associated tube opening upon power failure (or deactivation of the actuator), the second actuator 114 may alternatively be configured to close the associated tube opening upon power failure or deactivation of the actuator. In another variation, the occlusion system may be configured such that the tube opening associated with the first actuator 112 is open when the associated member 116 and/or anvil 128 are spaced away from the actuator 112 and closed when the member 116 and/or anvil 128 are closer to the actuator 112. In yet another variation, the occlusion system may be configured such that the tube opening associated with the second actuator 114 is closed when the associated member 118 and/or anvil 130 are spaced away from the actuator 114 and open when the associated member 118 and/or anvil 130 are closer to the actuator 114. Aspects of each of these various embodiments may be employed in combination with aspects of the other embodiments and/or the illustrated embodiment.

Figure 5:
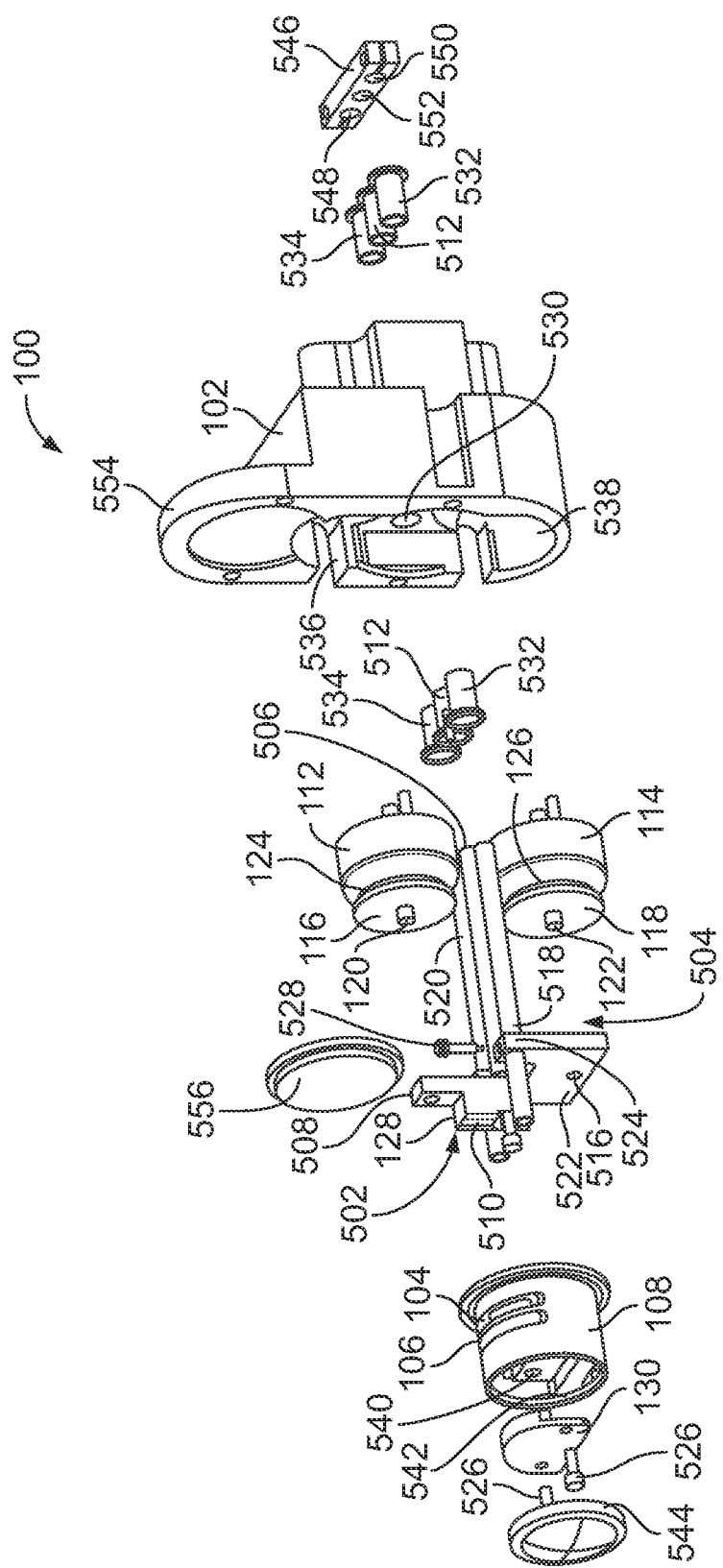
FIG. 5 is an exploded view of the occlusion device of FIGS. 1-4.

FIG. 5 is an exploded view of system 100, including housing 102, solenoids or actuators 112 and 114, openings 104 and 106, members 116 and 118, linear shafts 120 and 122, springs 124 and 126, anvils 128 and 130, and clamp head 108.

FIG. 5 also illustrates that in some examples, the example system 100 includes a first alignment assembly 502 and a second alignment assembly 504. The alignment assemblies 502 and/or 504 enable linear movement of the linear shafts 120 and 122 to be delivered to the respective anvils 128 and 130 and for any resultant loads and/or moments created when compressing the tubes in the tube openings 104 and 106 to be absorbed and to not affect the solenoids 112 and 114.

In some examples, the first alignment assembly 502 includes the first anvil 128, the linear shaft 120 and/or a first guide or alignment shaft 506. A first end or portion 508 of the first anvil 128 receives and/or is otherwise coupled to the linear shaft 120 and a second end or portion 510 of the first anvil 128 is coupled to the first alignment shaft 506.

In operation, to enable the first anvil 128 to substantially linearly move and/or apply linear forces to the tube(s) positioned in the tube opening 104, as the linear shaft 120 moves the first anvil 128, the first alignment shaft 506 is moved within an aperture (not shown) defined by the housing 102 and/or relative to bearings 512 positioned within the housing 102. A differently configured first alignment assembly may be employed without departing from the scope of the present disclosure, and the occlusion system may also be practiced without a first alignment assembly.

In some examples, the second alignment assembly 504 includes a plate or member 516, the linear shaft 122, and/or second and third guides or alignment shafts 518 and 520. A first end or portion 522 of the plate 516 receives and/or is otherwise coupled to the linear shaft 122 and a second end or portion 524 receives the second and third alignment shafts 518 and 520. The second anvil 130 may be coupled to the alignment shafts 518 and 520 by fasteners 526. In some examples, the plate 516 receives fasteners (only one of which is shown) 528 to secure and/or couple the second and third alignment shafts 518 and 520 relative to the plate 516. The fasteners 528 may extend through holes or apertures of the second and third alignment shafts 518 and 520 and threadably engage the plate 516.

In operation, to enable the second anvil 130 to substantially linearly move and/or apply linear forces to the tube(s) positioned in the tube opening 106, as the linear shaft 122 moves the plate 516, the shafts 518 and 520 are moved within respective apertures (only one of which is shown) 530 defined by the housing 102 and/or relative to bearings 532 and 534 positioned within the housing 102. Movement of the plate 516 and the shafts 518 and 520 in turn moves the second anvil 130 to which the shafts 518 and 520 are coupled. A differently configured second alignment assembly may be employed without departing from the scope of the present disclosure, and the occlusion system may also be practiced without a second alignment assembly.

In some examples, to assemble the system 100, the bearings 512, 532, and 534 and the solenoids 112 and 114 may be positioned in respective apertures 530, 536, and 538 defined by the housing 102. The alignment shafts 506, 518, and 520 may then be positioned through the respective bearings 512, 532, and 534. The plate 516 may be positioned on the second and third alignment shafts 518 and 520 and/or the linear shaft 122 such that the second and third alignment shafts 518 and 520 extend through the plate 516 and the linear shaft 122 is coupled to the plate 516. The second and third alignment shafts 518 and 520 may be coupled to the plate 516 by the fasteners 528 or other suitable connection means.

The first linear shaft 120 and the first alignment shaft 506 may then be coupled to the first anvil 128. The clamp head 108 may be positioned on the system 100 such that the first anvil 128 is at least partially positioned within the clamp head 108 on a first side of the divider 110. The second and third alignment shafts 518 and 520 may be positioned through apertures (only one of which is shown) 540 of the clamp head 108 to enable the second anvil 130 to be coupled to the alignment shafts 518 and 520 via the fasteners 526. The second anvil 130 may be positioned on a second side of the divider 110 (opposite the first side of the divider 110) and at least partially in an aperture 542 of the clamp head 108. After the second anvil 130 is coupled to the second and third alignment shafts 518 and 520, a cap 544 may be received by the clamp head 108 to at least partially cover the second anvil 130.

In some examples, to limit the movement of the second anvil 130, a stop 546 may be coupled to the second and third alignment shafts 518 and 520. The stop 546 may include clamps and/or apertures 548 and 550 that receive the third and second alignment shafts 520 and 518, respectively. Fasteners may be used to couple the stop 546 to the second and third alignment shafts 518 and 520. An aperture and/or clearance hole 552 may receive the first alignment shaft 506. The first alignment shaft 506 may be movable relative to the stop 546.

While the example system 100 is illustrated with an extension 554 and corresponding plate 556 to cover an opening of some blood collection and/or processing systems, it is also within the scope of the present disclosure for the example system 100 to omit the extension 554 and/or the plate 556. While the alignment shafts 506, 518, and 520 are depicted as being substantially parallel to one another, the alignment shafts 506, 518, and/or 520 may be differently arranged. While the alignment shafts 506, 518, and 520 are depicted as being positioned between the first and second solenoids 112 and 114, the alignment shafts 506, 518, and/or 520 and/or the first and second solenoids 112 and 114 may be differently positioned.

Figure 7:
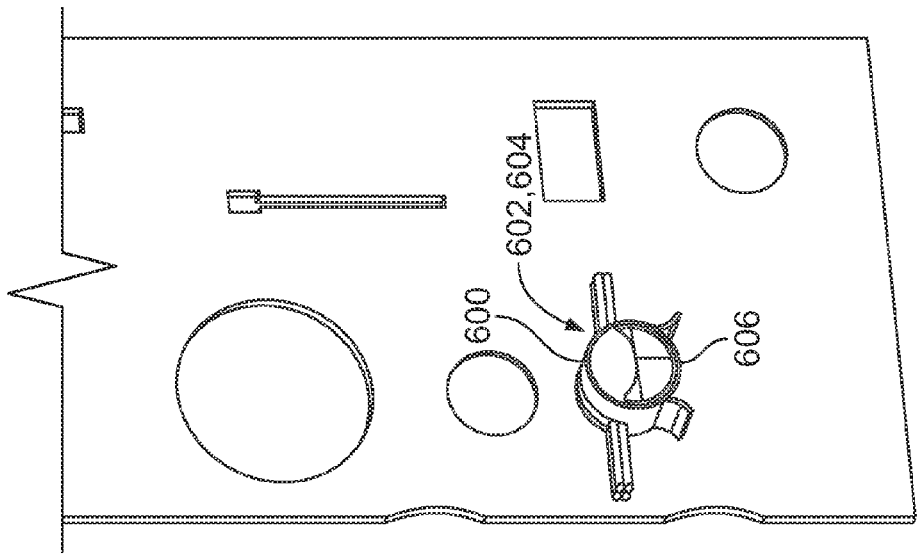
FIG. 7 is a perspective view of the tube carrier of FIG. 6, in a different position or condition.
Figure 6:
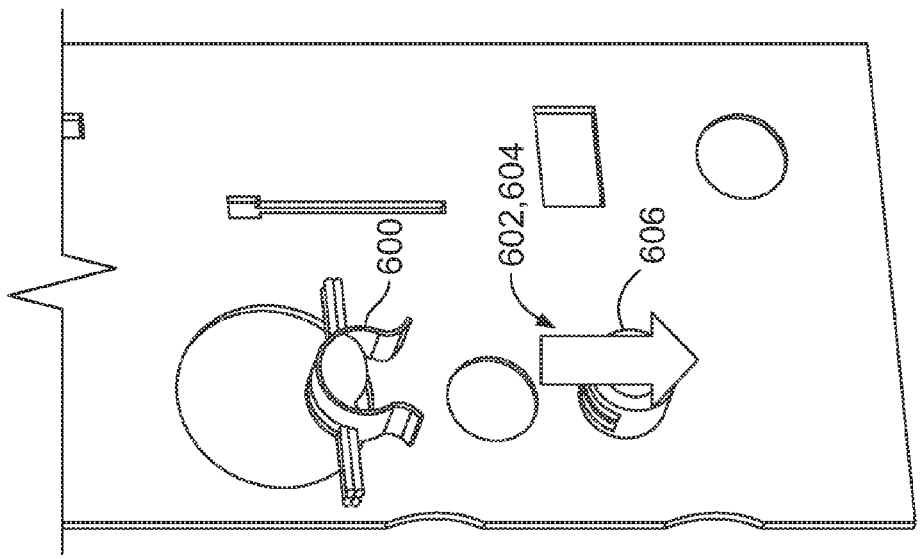
FIG. 6 is a perspective view of an example tube carrier according to an aspect of the present disclosure, which may be used in combination with occlusion devices, including occlusion devices of the type described herein.
Figure 8:
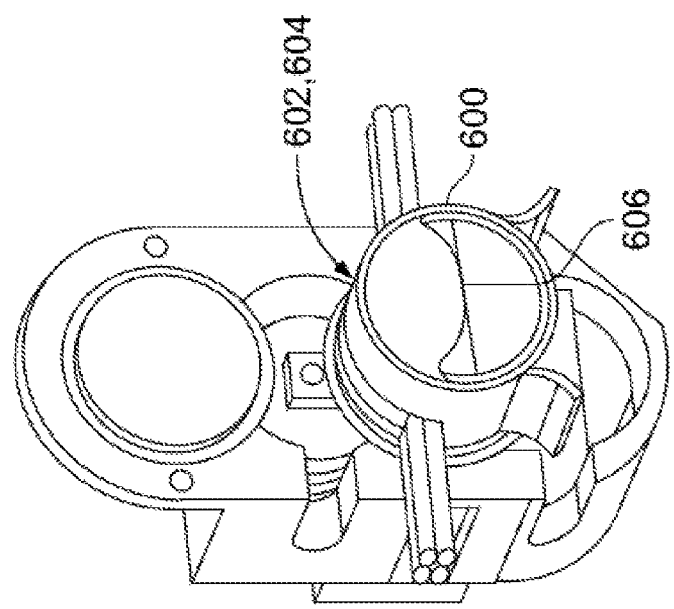
FIG. 8 is a perspective view of the tube carrier of FIGS. 6-7 and tubing coupled to the occlusion device of FIGS. 1-5.

FIGS. 6-8 illustrate another aspect of the present disclosure, which may be advantageous when the system 100 is incorporated into a blood collection assembly or the like. FIG. 6 shows a tubing carrier 600 from a blood collection disposable kit, such as an AMICUS® kit, ALYX® kit, AUTOPHERESIS-C® kit, etc., positioned above a clamp head 606. FIGS. 7 and 8 show tubing carrier 600 loaded onto clamp head 606 (corresponding generally to clamp head 108 of FIGS. 1-5) so that the tubing is positioned in tube openings 602 and 604 (corresponding generally to tube openings 104 and 106 of FIGS. 1-5). During a blood collection/separation procedure, a user may position a tubing carrier 600 from a disposable kit onto clamp head 606 for operation (e.g., fluid path occlusion/restriction) as described above in connection with FIGS. 1-4.

Figure 9:
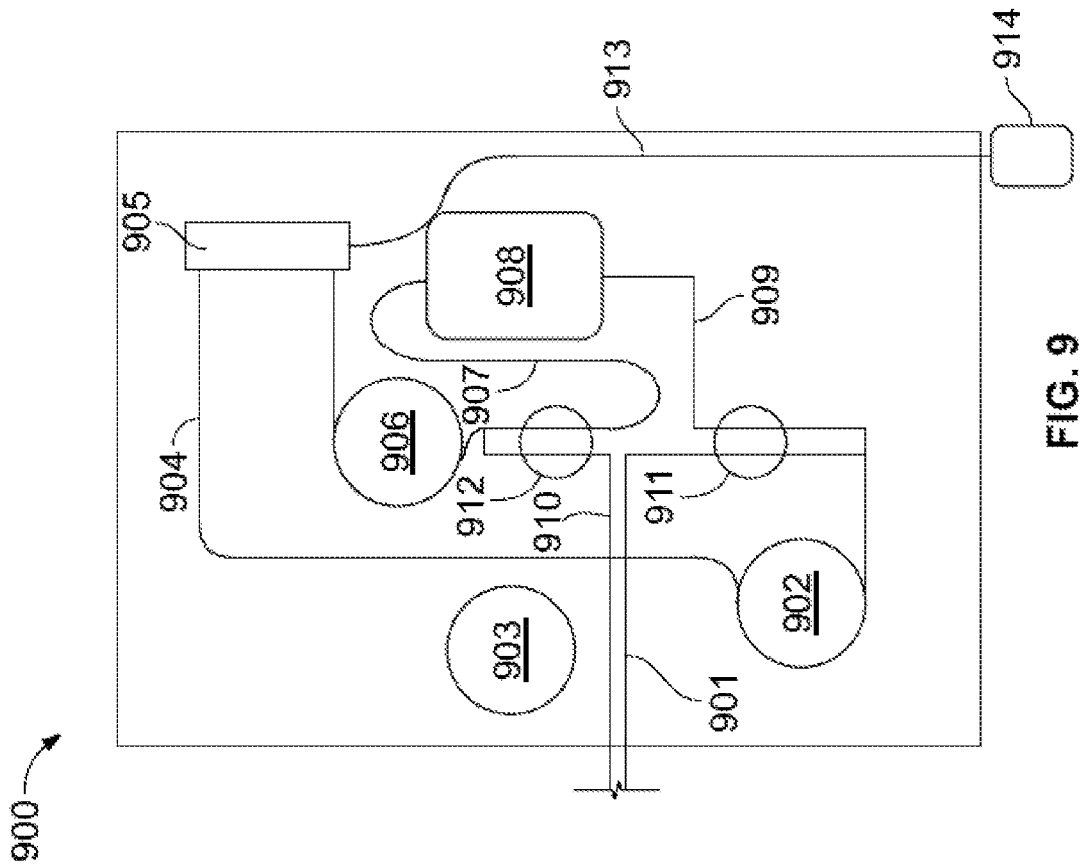
FIG. 9 is a schematic view of an example collection apparatus configuration for plasmapheresis, according to an aspect of the present disclosure.

FIG. 9 illustrates an example collection apparatus configuration 900 for fluid separation, such as plasmapheresis. The operation of the example system and/or any of the other examples disclosed herein may be driven by an external program or other stimulus. The example apparatus 900 includes a blood source draw line 901, a blood pump 902, an anticoagulant (AC) pump 903, a continuous processing line 904, a PLASMACELL-C® separator 905 (or other suitable separator/centrifuge), a red cell pump 906, an in process line 907, an in process reservoir 908, a return processing line 909, a blood source return line 910, binary clamps 911 and 912 (such as the embodiments described in connection with FIGS. 1-8), a plasma line 913, and a plasma collection container 914. The system 900 is explained in further detail below in conjunction with a draw cycle configuration 1000 (FIG. 10) and return cycle configuration 1100 (FIG. 11).

Figure 10:
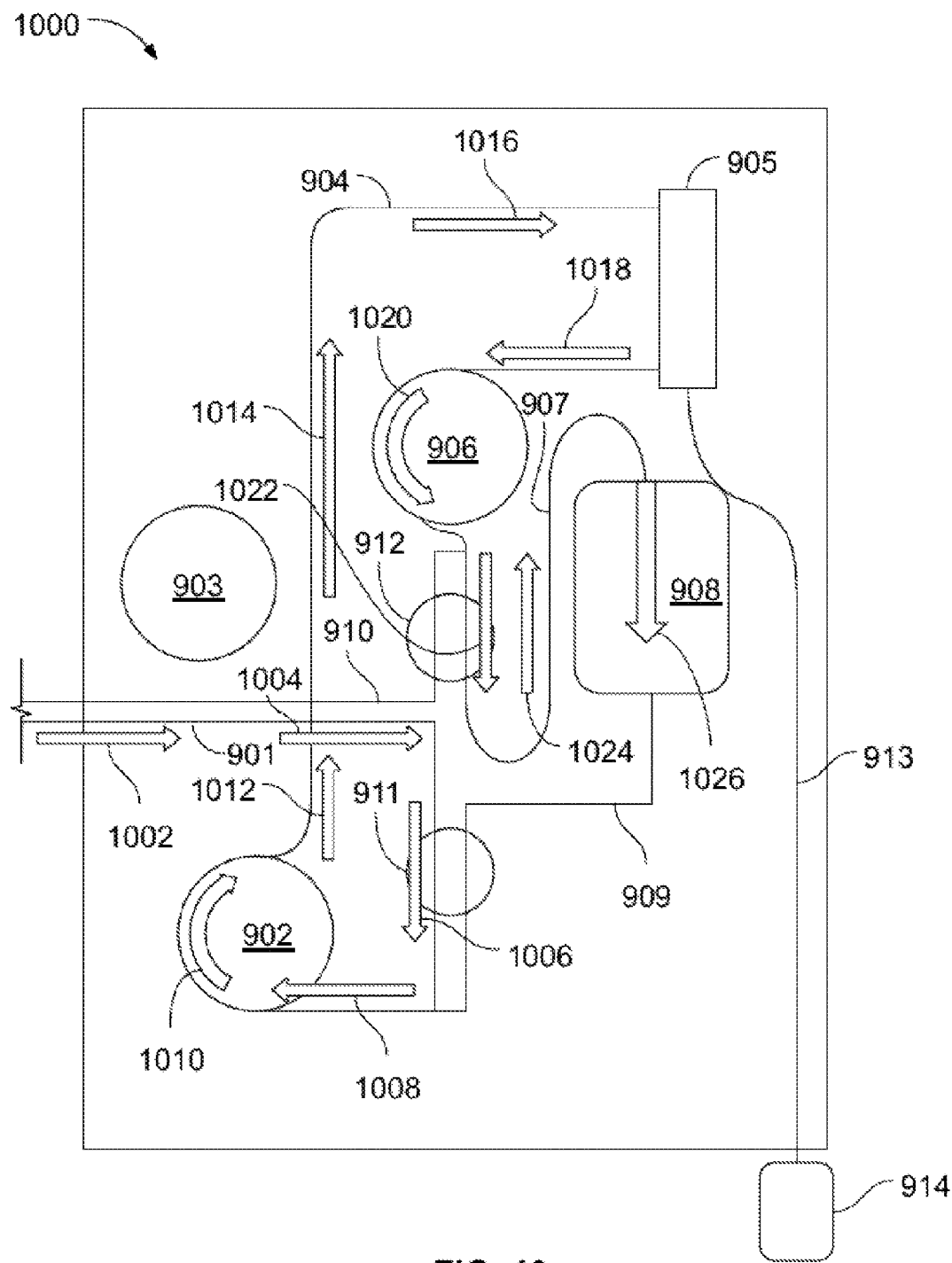
FIG. 10 illustrates an example draw cycle configuration using the collection apparatus of FIG. 9.
Figure 11:
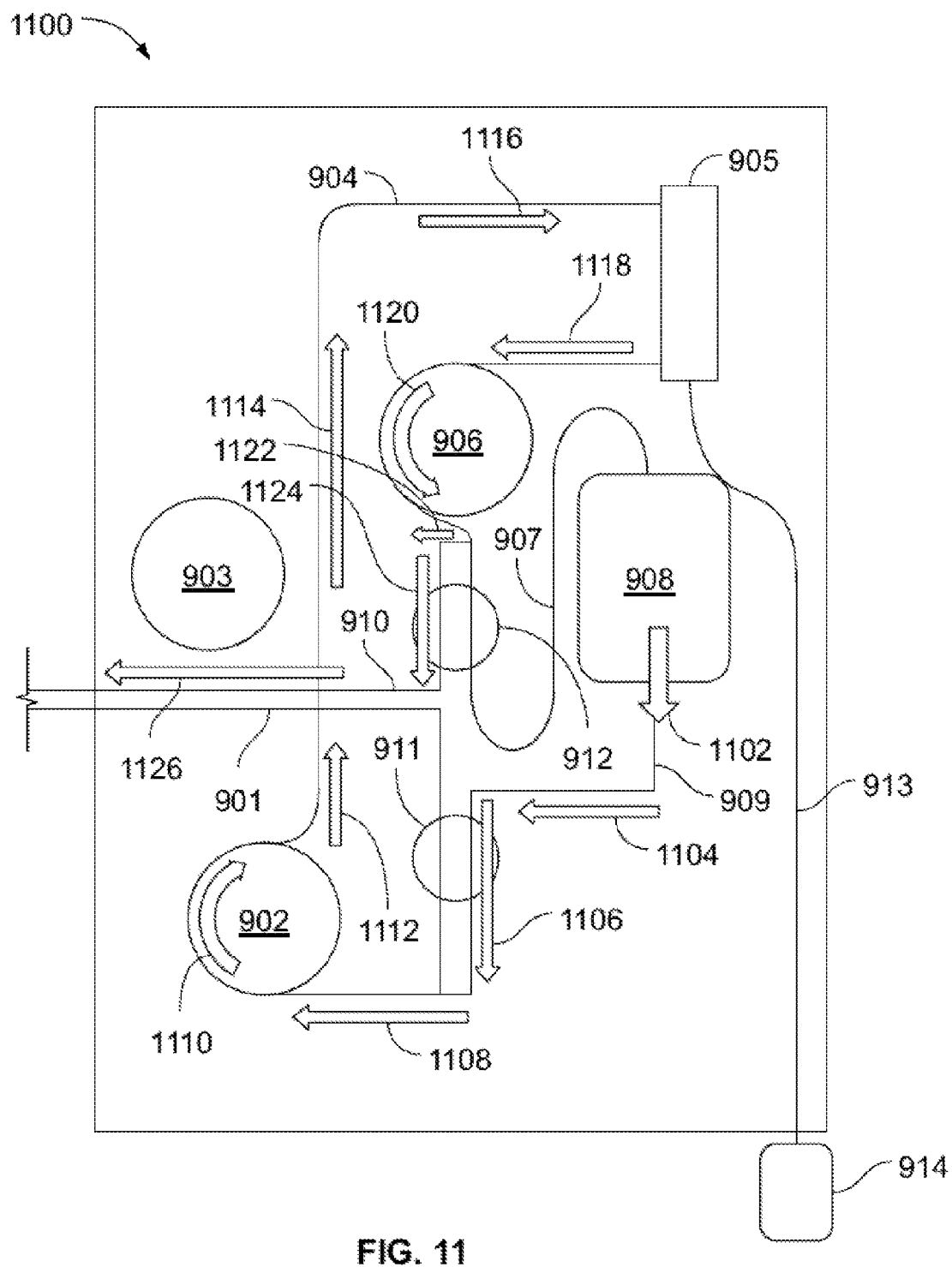
FIG. 11 illustrates an example return cycle configuration using the collection apparatus of FIG. 9.

FIG. 10 illustrates an example draw cycle configuration of a collection on return apparatus 1000. The example apparatus 1000 includes a blood source draw line 901, a blood pump 902, an AC pump 903, a continuous processing line 904, a PLASMACELL-C® separator 905 (or other suitable blood separation mechanism), a red cell pump 906, an in process line 907, an in process reservoir 908, a return processing line 909, a blood source return line 910, binary clamps 911 and 912, a plasma line 913, and a plasma collection container 914.

During a draw cycle 1000, depicted in FIG. 10, as indicated by arrows 1002, 1004, 1006, and 1008, blood is continuously drawn into the system from a donor or other blood source by the blood pump 902 (as indicated by arrow 1010) via the blood source draw line 901. The blood source draw line 901 is in an open position of the binary clamp 911 to enable blood flow while the return processing line 909 is in a closed position of the binary clamp 911 to prevent blood flow. For example, if the occlusion system 100 of FIGS. 1-5 was used to provide the binary clamp 911, the occlusion system 100 could be in the condition illustrated in FIG. 4 during the draw cycle, with the blood source draw line 901 in the open tube opening 104 and the return processing line 909 in the closed tube opening 106.

As indicated by the flow of arrows 1010, 1012, 1014, and 1016, the blood pump 902 passes the whole blood (WB) through the continuous processing line 904 into an inlet of the fluid separator 905. Within the separator 905, the WB is separated by a spinning membrane filtration device or other suitable separation means. Plasma is collected in the plasma collection container 914 via the plasma line 913 and, at 1018, high hematocrit (HCT) blood (e.g., approximately 58% HCT) is pulled out of the separator 905 by the red cell pump 906 (as indicated by arrow 1020) and, as indicated by arrows 1022, 1024, and 1026, placed into the in process reservoir 908 via the in process line 907. The in process line 907 is in the open position of the binary clamp 912 to enable blood flow while the blood source return line 910 is in the closed position of the binary clamp 912 to prevent blood flow. For example, if the occlusion system 100 of FIGS. 1-5 was used to provide the binary clamp 912, the occlusion system 100 could be in the condition illustrated in FIG. 2 during the draw cycle, with the blood source return line 910 in the closed tube opening 104 and the in process line 907 in the open tube opening 106.

The draw cycle may continue until the in process reservoir 908 is filled (or at least partially filled) with high HCT blood. Once the in process reservoir 908 is at least partially filled, both binary clamps 911 and 912 may be caused to instantaneously (or at least substantially instantaneously given some system delay) reverse their opened and closed positions (i.e., with the binary clamp 911 switching from the condition of FIG. 4 to the condition of FIG. 2 and the binary clamp 912 switching from the condition of FIG. 2 to the condition of FIG. 4) to divert blood flow, enabling the system 1000 to transition to a return cycle.

FIG. 11 illustrates an example return cycle configuration in a collection on return apparatus 1100. The example apparatus 1100 includes a blood source draw line 901, a blood pump 902, an AC pump 903, a continuous processing line 904, a fluid separator 905, a red cell pump 906, an in process line 907, an in process reservoir 908, a return processing line 909, a blood source return line 910, binary clamps 911 and 912, a plasma line 913, and a plasma collection container 914.

During a return cycle 1100, depicted in the example of FIG. 11, high HCT blood is continuously (or at least substantially continuously accounting for some equipment delay) pumped out of the in process reservoir 908, as indicated by arrows 1102, 1104, 1106, and 1108, by the blood pump 902 via the return processing line 909. The return processing line 909 is in the open position of the binary clamp 911 to enable blood flow while the blood source draw line 901 is in the closed position of the binary clamp 911 to prevent blood flow. For example, if the occlusion system 100 of FIGS. 1-5 was used to provide the binary clamp 911, the occlusion system 100 could be in the condition illustrated in FIG. 2 during the return cycle, with the blood source draw line 901 in the closed tube opening 104 and the return processing line 909 in the open tube opening 106.

As indicated by arrows 1110, 1112, 1114, and 1116, the blood pump 902 passes the high HCT blood through the continuous processing line 904 into an inlet of the fluid separator 905. Within the separator 905, the high HCT blood is again separated by the spinning membrane filtration device or other suitable separation means. Plasma is collected in the plasma collection container 914 via the plasma line 913 and, as indicated by 1118, concentrated red cells (e.g., approximately 68% HCT) are pulled out of the separator 905 by the red cell pump 906. As indicated by 1120, 1122, 1124, and 1126, the red cell pump 906 then passes the concentrated red cells through the blood source return line 910 and directly back to the blood source. The blood source return line 910 is in the open position of the binary clamp 912 to enable blood flow while the in process line 907 is in the closed position of the binary clamp 912 to prevent blood flow. For example, if the occlusion system 100 of FIGS. 1-5 was used to provide the binary clamp 912, the occlusion system 100 could be in the condition illustrated in FIG. 4 during the return cycle, with the blood source return line 910 in the open tube opening 104 and the in process line 907 in the closed tube opening 106.

The return cycle may continues until the in process reservoir 908 is emptied (or at least partially emptied). Once the in process reservoir 908 is at least partially emptied, both binary clamps 911 and 912 may be caused to instantaneously (or at least substantially instantaneously) reverse their opened and closed positions (i.e., with the binary clamp 911 switching from the condition of FIG. 2 to the condition of FIG. 4 and the binary clamp 912 switching from the condition of FIG. 4 to the condition of FIG. 2) to divert blood flow, enabling the system 1100 to transition to a draw cycle. Transition draw and return cycles may continue until the plasma collection target is met. Collecting plasma on both draw and return helps reduce system idle time and increase speed time of plasma collection from a blood source. In certain examples, the first collection cycle begins on a draw and the last collection cycle ends on a return to help ensure excess blood does not remain in the system, for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A clamping apparatus for use with a fluid flow device, comprising:
a clamp head at least partially defining first and second tube openings each to receive tubing;
a first actuator coupled to a first flow control member and positioned on a side of the first and second tube openings, with the first flow control member being configured to be movable via the first actuator relative to the first tube opening to control fluid flow through a first tube located in the first tube opening; and
a second actuator coupled to a second flow control member, with the second flow control member being movable via the second actuator relative to the second tube opening to control fluid flow through a second tube located in the second tube opening, wherein
the second actuator is positioned on the same side of the first and second tube openings as the first actuator, and one of the tube openings is positioned between the actuators and the other tube opening.

2. The clamping apparatus of claim 1, wherein the first and second flow control members are independently movable.

3. The clamping apparatus of claim 1, wherein the clamp head comprises a divider to substantially separate the first tube opening from the second tube opening.

4. The clamping apparatus of claim 3, wherein the first flow control member is on a first side of the divider and the second flow control member is on a second side of the divider.

5. The clamping apparatus of claim 1, further comprising a housing in which the first and second actuators are at least partially positioned and to which the clamp head is operably coupled.

6. The clamping apparatus of claim 1, further comprising a guide coupled to the first flow control member to at least partially linearly guide movement of the first flow control member.

7. The clamping apparatus of claim 6, wherein the guide comprises an alignment shaft.

8. The clamping apparatus of claim 6, wherein the guide is received by an aperture of a housing, with the housing being operably coupled to the clamp head.

9. The clamping apparatus of claim 6, wherein the first actuator is coupled to a first portion of the first flow control member and the guide is coupled to a second portion of the first flow control member.

10. The clamping apparatus of claim 1, further comprising guides coupled to the second flow control member to at least partially linearly guide movement of the second flow control member.

11. The clamping apparatus of claim 10, wherein the guides comprise alignment shafts.

12. The clamping apparatus of claim 10, wherein the guides extend through a divider of the clamp head to enable the second flow control member to be coupled to the guides, with the divider being configured to substantially separate the first tube opening from the second tube opening.

13. The clamping apparatus of claim 10, wherein the guides are received by apertures of a housing, with the housing being operably coupled to the clamp head.

14. The clamping apparatus of claim 10, further comprising a plate having a first portion to which the guides are coupled and a second portion to which the second actuator is coupled.

15. The clamping apparatus of claim 10, wherein the guides are positioned between the first and second actuators.

16. The clamping apparatus of claim 1, wherein the first and second flow control members comprise clamping anvils.

17. The clamping apparatus of claim 1, wherein the first and second tube openings are externally accessible to enable the tubing to be at least partially positioned therein.

18. The clamping apparatus of claim 1, wherein the first flow control member is movable in a first direction to decrease fluid flow through the first tube opening and the second flow control member is movable in a second direction to decrease fluid flow through the second tube opening, with the first direction being opposite the second direction.

19. A system for occluding fluid in one or more fluid pathways comprising:
- a first tube opening for receiving a portion of a first tube comprising a first fluid pathway;
- a second tube opening for receiving a portion of a second tube comprising a second fluid pathway;
- a first actuator coupled to a first linear drive mechanism and positioned on a side of the first and second tube openings;
- a second actuator coupled to a second linear drive mechanism;
- a first anvil coupled to the first linear drive mechanism; and
- a second anvil coupled to the second linear drive mechanism, wherein
  - the first and second actuators are positioned on the same side of the first and second tube openings,
  - the first actuator is configured to move the first linear drive mechanism and the first anvil in a first direction to restrict the first tube opening and at least partially occlude the first tube opening, and
  - the second actuator is configured to move the second linear drive mechanism and the second anvil in a second direction opposite to the first direction to restrict the second tube opening and at least partially occlude the second tube opening.

\* \* \* \* \*